United States Patent

Melendez et al.

[11] Patent Number: 6,111,652
[45] Date of Patent: Aug. 29, 2000

[54] HIGH THROUGHPUT SURFACE PLASMON RESONANCE ANALYSIS SYSTEM

[75] Inventors: Jose L. Melendez, Plano; Donald I. Stimpson, Dallas, both of Tex.

[73] Assignee: Texas Instruments Incorporated, Dallas, Tex.

[21] Appl. No.: 09/348,598

[22] Filed: Jul. 6, 1999

Related U.S. Application Data

[60] Provisional application No. 60/092,906, Jul. 14, 1998.

[51] Int. Cl.[7] .............................. G01N 21/55; H01J 3/14
[52] U.S. Cl. ...................... 356/445; 356/369; 250/216; 250/225; 250/239
[58] Field of Search .................... 356/445, 318, 356/446, 317, 345, 73, 369; 250/216, 225, 239

[56] References Cited

U.S. PATENT DOCUMENTS

| | | | |
|---|---|---|---|
| 5,313,264 | 5/1994 | Ivarsson et al. ........................ | 356/73 |
| 5,485,277 | 1/1996 | Foster ........................................ | 356/445 |
| 5,492,840 | 2/1996 | Malmqvist et al. ..................... | 436/518 |
| 5,898,503 | 4/1999 | Keller et al . .......................... | 356/445 |
| 5,912,456 | 6/1999 | Melendez et al. ...................... | 356/369 |

FOREIGN PATENT DOCUMENTS

| | | |
|---|---|---|
| 0 797 091 A1 | 9/1997 | European Pat. Off. . |
| 0 846 946 A2 | 6/1998 | European Pat. Off. . |
| 95/22754 | 8/1995 | WIPO . |

*Primary Examiner*—Frank G. Font
*Assistant Examiner*—Roy M. Punnoose
*Attorney, Agent, or Firm*—W. Daniel Swayze, Jr.; W. James Brady, III; Frederick J. Telecky, Jr.

[57] ABSTRACT

An apparatus and method for high throughput surface plasmon resonance (SPR) sensor subarray comprising two or more SPR sensor subarrays (10) having a target layer on an SPR layer (22), wherein the SPR sensor subarrays (10) are exposed to a solution until a baseline measurement is attained, is disclosed. Once the SPR sensor subarrays (10) have attained baseline, the SPR sensor subarrays (10) are used to determine the interaction properties between said SPR sensor subarray and a test entity.

20 Claims, 6 Drawing Sheets

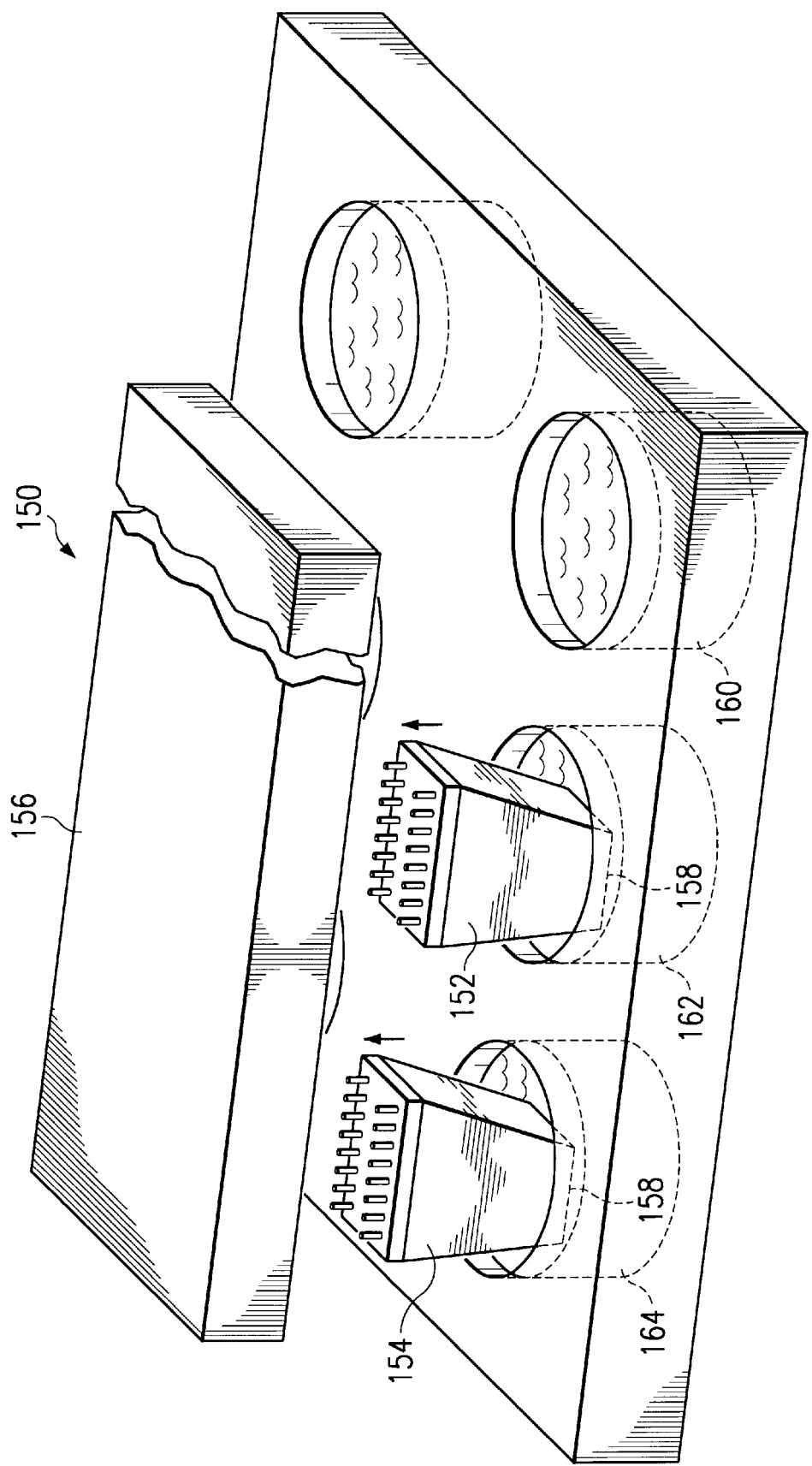

HIGH THROUGHPUT SURFACE PLASMON RESONANCE ANALYSIS SYSTEM

This application claims benefit of Provisional application Ser. No. 60/092,906 filed Jul. 14, 1998.

TECHNICAL FIELD OF THE INVENTION

The present invention relates in general to the field of surface plasmon resonance (SPR) based sensors, and more particularly, to a high throughput SPR analysis apparatus and system for qualifying or quantifying parameters descriptive of molecular binding events or detecting a test within a sample.

BACKGROUND OF THE INVENTION

Without limiting the scope of the invention, its background is described in connection with optically based sensor systems, as an example.

Heretofore, in this field, the development of surface plasmon resonance-based sensors for the analysis of specific molecular interactions within specimens or samples have required expensive equipment, highly trained personnel, large samples, and days to weeks to complete. While molecular interaction and binding analysis has been an active area of research, present systems are limited in the range of applications and are unable to be used to analyze large numbers of specific compounds.

An active area of sensor development has been the use of an optical phenomenon known as surface plasmon resonance (SPR). Biosensors of this type, such as the BIAcore line from Biacore, Upsala, Sweden, are available for use in research and development. Two factors limiting the general use of SPR biosensors, however, are the relatively high cost of developing and using specific biosensors and the inability to increase the sample throughput. One solution to the inability to increase sample throughput has been to purchase a number of SPR-based machines that are run in parallel. The purchase and operation of large numbers of these machines for true high throughput testing is, however, prohibitive.

SUMMARY OF THE INVENTION

The present inventors have recognized that the most time consuming step in a surface plasmon resonance analyses event is obtaining a baseline prior to test element analysis. The problems associated with increasing the speed of baselining has led to approaches that include changing buffers and increasing temperature. The problem with these approaches is they are time consuming and lead to the need to highly purify the target elements so as to avoid non-specific surface interactions by impurities in the preparation. Another problem is the difficulty in attaching the target element to an SPR metal on an SPR layer. The problem is two-fold: first, the target element has to be attached to the SPR layer; and second, once the target element has been exposed to the sample containing a test entity, the test entity must often be removed from the target element without removing the target element from the SPR layer. Yet another problem is the need to prepare and treat the gold surface to prevent non-specific binding.

More particularly, the present invention is an SPR sensor subarray including a substrate having first and second surfaces. A light source is disposed coupled to the first surface of the substrate, and adjacent the light source a photodetector is also coupled to the substrate. A housing disposed on the first surface of the substrate has a surface that is subdivided into four or more target layer areas, wherein each of the target layer areas are predisposed to receive light from the light source and direct it towards a portion of the photodetector.

Detection of interaction parameters between the SPR sensor subarray and multiple test entities occurs through the target layer area. The target layer area has disposed thereon a "surface plasmon resonance layer", such as a metal. A "target layer" is disposed on the surface plasmon resonance layer, which adds binding capabilities to the target layer area. An example of a target layer can be an antibody layer. The antibody layer can be covalently bound to the surface plasmon resonance layer. In the antibody example, the antigen of the antibody is termed herein the "test element", as it interacts with the test layer of the test layer area of the SPR sensor subarray.

The present invention is also a high throughput apparatus for qualifying or quantifying parameters descriptive of molecular binding events, or for detecting the presence of a target element, including SPR sensor subarrays having target elements and appropriate reference elements, wherein the first sensor subarray is exposed to a solution until a baseline measurement is attained and a second SPR sensor subarray that has already reached baseline is used to detect the presence of a test entity in a sample at about the same time. The apparatus of the present invention may also include a plate having two or more wells in fluid communication with the SPR sensor subarray, wherein one of the wells contains a sample that is exposed to the SPR sensor subarray qualifying or quantifying parameters descriptive of molecular interactions events or to determine the existence of a test element in the sample. The apparatus may also have one or more SPR sensor subarrays used to determine if a baseline condition has been attained, in-line that contact solutions being used for baselining or detection at about the same time. In another embodiment, the SPR sensor arrays include specificity elements that interact with a test entity to produce a change in surface plasmon resonance.

In one embodiment, the present invention allows for the use of one or more staggered SPR sensor subarrays, which act in parallel, to detect target elements. For example, 96 SPR sensor subarrays can be formed into a single SPR sensor array that contains at least one target layer on, e.g., a four channel SPR sensor layer. Each subarray of the SPR sensor array can be exposed to a different target element from a different sample in, e.g., a 96-well plate by, e.g., "dipping" the protrusions of an SPR sensor subarray into the samples in the wells. The test layer area of each of the 96 SPR sensors in a subarray is made to contact an individual sample in the 96-well plate, and an output is measured over time. By contacting each sample of the 96-well plate using an SPR sensor subarray, 96 different samples can be analyzed for the presence or absence of target element binding, concurrently and in real time. By bringing some or all of the SPR sensor surfaces of the SPR sensor subarray in contact with the sample in a well, the need for expensive robotics and fluidics for sample transfer and sensor exposure is eliminated. Depending on the sample number and quantity, the number of SPR sensors that form the sub array can be increased or decreased.

One advantage of the SPR sensor subarrays is that the output is obtained in parallel for a large number of samples, reducing the time required per sample analysis, which is one limitation of current SPR sensor models that operate in series. Furthermore, the use of SPR sensors for the subarray permits the for a qualitative analysis of the interaction between the portion of the SPR sensor surface that has the recognition element and the target element. Furthermore, the quantity and stability of molecular binding events can also be analyzed.

Another embodiment of the invention is a method of high throughput SPR detection comprising the steps of, baselining an SPR sensor subarray to obtain a baselining output for each sensor in the subarray, exposing the SPR sensor subarray to a sample containing a target element to obtain a target element output for each sensor in the subarray, and comparing the target element output with the previous baselining output for each sensor in the subarray, wherein the difference between the target element output and the baselining output for each sensor in the subarray is the level of interaction between a target element and the SPR sensor layer. Interaction parameters can be calculated based on the difference between the baseline and the sample output for the SPR sensor subarray measured over time.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 7 shows the output as read from individual SPR sensor subarrays that form a linear sensor array;

DETAILED DESCRIPTION OF THE INVENTION

Figure 1:
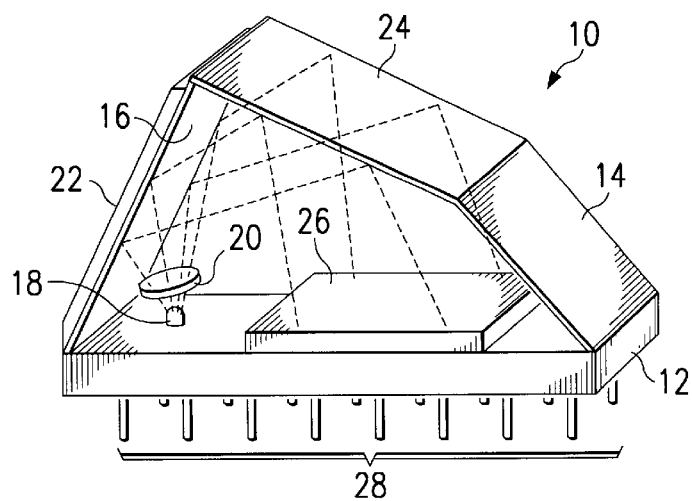
FIG. 1 is a three dimensional view of an SPR sensor subarray.

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention and do not delimit the scope of the invention.

The present invention uses a molecular target structure that is disposed about a gold surface, which form the target layer of an SPR sensor. The molecular target structure can, e.g., covalently immobilized about the gold surface. The target layer has the characteristic quality of binding to a specific test entity or group of test entities. The target structure may be further defined as a specific target element, which may be for example, an antibody, a lectin, a hormone receptor, a nucleic acid, a carbohydrate, a lipid, or any antigen, hormone or other molecule. The target layer for use with the SPR sensors that form a subarray are used in a high throughput SPR detection based system, which may be further defined as including an intermediary adaptive layer capable of reversibly binding one or more target elements with different biochemical binding properties, and a specific target element bound to the intermediary adaptive layer.

A wide variety of test entities may be used to direct the interactions of the SPR sensor subarrays. The molecular interactions that can be analyzed will generally be specific, but in some cases may be non-specific. For example, the test entities may be an antigen and the target element can be an antibody specific to the antigen. Alternatively, the antibody may cross-react with the antigen. The invention is not to be taken as limited to assays of antibodies or antigens, as such, examples of test entities that may be analyzed by the apparatus and method of the present invention are given in Table 1 below, together with an indication of a suitable specific binding partner in each instance. Furthermore, as will be appreciated by one of skill in the art, the test entity and target element can be interchanged.

TABLE 1

| Test Entity | Target element |
| --- | --- |
| antigen | specific immunoglobulin |
| immunoglobulin | antigen |
| hormone | hormone receptor |
| hormone receptor | hormone |
| polynucleotide strand | complementary polynucleotide strand |
| avidin | biotin |
| biotin | avidin |
| protein A | immunoglobulins |
| protein G | IgG immunoglobulins |
| immunoglobulin | Protein A or Protein G |
| enzyme or inhibitor | enzyme cofactor (substrate) |
| enzyme cofactor or inhibitor | enzyme (substrate) |
| lectins | specific carbohydrate |
| specific carbohydrate | lectins |
| microorganism proteomics | antibody |

The SPR detector array of the invention has broad applicability but in particular may be used to analyze drug candidates analyze: hormones, including peptide hormones (e.g. thyroid stimulating hormone (TSH), luteinizing hormone (LH), human chorionic gonadotropin (hCG), follicle stimulating hormone (FSH), insulin and prolactin) or non-peptide hormones (e.g. steroid hormones such as cortisol, estradiol, progesterone and testosterone, or thyroid hormones such as thyroxine (T4) and triiodothyronine), proteins (e.g. carcinoembryonic antigen (CEA) and alphafetoprotein (AFP)), drugs (e.g. digoxin), sugars, toxins, vitamins, viruses such as influenza, parainfluenza, adeno-, hepatitis, respiratory and AIDS viruses, or microorganisms or cardiac markers (e.g. creatine kinase, myoglobin, troponin I, troponin T).

It will be understood the term "antibody" as used herein includes within its scope, any of the various classes or sub-classes of immunoglobulin, e.g. IgG, IgA, IgM, or IgE derived from any of the animals conventionally or unconventionally used as a source of sera, e.g. sheep, rabbits, goats or mice to name a few, (b) monoclonal antibodies whether produced by cell fusion with immortalized cells, by recombinant techniques in eukaryotic or prokaryotic cells, or (c) intact molecules or "fragments" of antibodies, monoclonal or polyclonal, the fragments being those which contain the binding region of the antibody, i.e. fragments devoid of the Fc portion (e.g. Fab, Fab', F(ab')$_2$) or fragments obtained by reductive cleavage of the disulphide bonds connecting the heavy chain components in the intact antibody so long as they retain antigen binding capabilities.

Likewise, other members of the immunoglobulin domain-containing proteins, e.g, T cell receptors, can be bound to an SPR layer to create the target layer of an SPR sensor subarray. Methods for the preparation of fragments of immunoglobulin domain-containing proteins, as well as other, chimeric proteins, and the like are well known in the art and will not be described herein.

The term "antigen" as used herein will be understood to include both naturally antigenic species (for example, proteins, bacteria, bacterial fragments, cells, cell fragments, carbohydrates, nucleic acids, lipids, and viruses, to name a few) and haptens, which may be rendered antigenic under suitable conditions and recognized by antibodies or antibody fragments.

The present invention provides a system for qualifying or quantifying parameters descriptive of molecular binding events or for detecting the presence of a target element that is, or is part of, a sample. SPR-based detection includes an optical structure having a substrate coated with a thin SPR layer of metal, the metal layer is itself coated with a target layer, which causes a surface plasmon resonance event on the SPR surface when it interacts with a binding partner, a partner that recognizes a target element, however, in some cases a non-specific interaction can also be measured. The choice of running solution, e.g., a running buffer, can be used to minimize non-specific interactions. One such method to prevent undesired non-specific interactions is to coat the portions of the SPR layer that are not coated with the target element with a blocking compound, e.g, bovine serum albumin when using an antibody as the target layer.

One example of a method of forming a target layer area of an SPR sensor subarray onto, e.g., a gold surface, is by forming a monolayer of long-chain alkanethiols with suitable reactive groups on one end of the molecule and a gold-complexing thiol on the other. The actual test entity binding molecules are attached directly to the alkanethiol monolayer or to a hydrogel layer. An example of hydrogel monolayer is carboxymethyl dextran, that is attached to the monolayer.

The purpose of providing an additional hydrogel layer over the alkanethiol monolayer is to favor normal protein interaction and function, which are disrupted by the thiol groups used for attaching proteins. The additional monolayer may also be necessary to provide a more hydrophilic environment at the gold surface than is provided by the monolayer alone. The presence of a hydrogel may also be necessary to reduce the non-specific binding of proteins on the gold surface and to stabilize the alkanethiol monolayer attachment to gold.

The general features of an integrally formed Surface Plasmon Resonance ("SPR") sensor subarray 10 is shown in FIG. 1. A substrate 12 provides a device platform for the optical and electronic components of the SPR sensor subarray 10. A light transmissive housing 14 is disposed on the substrate 12 and permits light 16 to traverse the housing 14. A light source 18 is preferably located above or within the substrate 12 and has an aperture allowing light 16 to pass. A polarizer 20 is located near the light source 18 to polarize passing light 16 which, in turn, continues through housing 14 and strikes a SPR layer 22, which is formed into individual SPR sensors. In one embodiment, the SPR layer 22 that is formed on an exterior surface of the housing 14 has multiple target layer areas. Each of the target layer areas may have, e.g., four channels. Furthermore, the SPR layer 22 can be made to have protrusions, wherein each protrusion represents a target layer area. Alternatively, an array of individual SPR sensors can be disposed on a mother-board to form a subarray of SPR sensors, or even a subarray of SPR sensor subarrays.

The configuration depicted in FIG. 1 achieves an optical surface phenomenon that can be observed when the polarized light is internally reflected from the interface between the SPR layer 22 before and after a sample of interest, i.e., a test entity, contacts the surface of the SPR layer 22 (not shown in FIG. 1). The change in surface plasmon resonance is detected, and can be used to analyze the interaction parameters of multiple entities or samples in concurrently and in real-time. The interaction parameters can include, e.g., what test entities bind the target layer, how much binds, how fast the binding occurs and how stable the interaction may be between the test entities and the target layer.

A variety of metals can be used to produce SPR layer 22. To sustain surface plasmon resonance a metal must have conduction band electrons capable of resonating with light of the appropriate wavelength and chemical compatibility with the chemistries needed to perform assays. Gold is one metal that can be used to form the SPR layer 22 onto which a target layer that provides the binding characteristics of sensor subarray, or individual sensors thereof, can be disposed. Other metals such as indium, sodium, copper, aluminum or silver may be used alone or in combinations depending on the wavelength used and the level of sensitivity required to form the SPR layer 22.

As shown, a mirrored surface 24 directs the light 16 reflected from the SPR layer 22 onto a detector area array 26, which senses illumination intensity of the reflected light 16. For optical radiation, a suitable detector array 26 can be two or more photodetector line arrays with a linear array of resolution n×1 consisting of n discrete photo sensing areas, or pixels or a single two-dimensional photodetector array device. Depending on the number of sensors that form the subarray, a photodetector can be selected that maximizes area and detection, e.g., a 1K or a 4K CCD detector. The choice of detector will generally depend on the wavelength of light selected for causing and detecting surface plasmon resonance. The size of the detector will generally depend on the size of the individual sensors that form the SPR sensor subarray and the level of resolution that is sought, as will be known to those of skill in the art of SPR.

Light energy striking a pixel generates electron-hole pairs in the region under the pixel. The field generated by the bias on the pixel causes the electrons to collect in an element while the holes are swept into the substrate. Each sensing area in the detector array 26 produces a signal output with a voltage that is proportional to the intensity of the radiation striking the detector array 26.

A lead frame 28 is coupled to the opposite side of the substrate 12 from the housing 14 and provides a signal pathway from the detector array 26 output. While a lead frame is depicted in the form of wires, one of skill in the art of semiconductor packaging will know that alternative electrical connectors, such as pads for solder bonding, can be used to maintain electrical connections between the electronics of the apparatus and subsequent electrical connection systems used in, e.g., capturing and analyzing data from the SPR sensor subarray 10. The lead frame 28 or solder balls can connect the SPR sensor subarray 10 to, e.g., mother- or sister-board.

Figure 2:
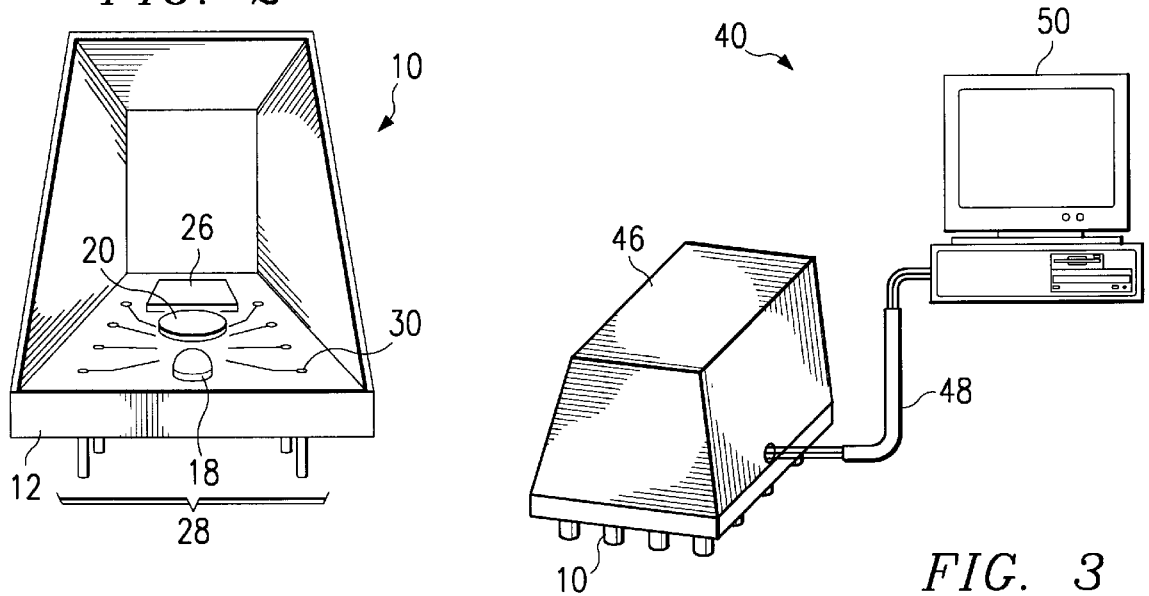
FIG. 2 is a isometric side view of an SPR sensor subarray.

FIG. 2 is an isometric side view of the SPR Sensor subarray 10. The SPR layer 22 has been removed so that the interior of the SPR sensor array 10 can be seen. The substrate 12 has disposed thereon the light 18 and polarizer 20 that is above the light 18. Adjacent to the light source 18 and the polarizer 20 on the substrate 12 are routing strips or lines 30 that connect to the lead frame 28. In FIG. 2, the detector area array 26 is used, which reflects the fact that the light 16 that is reflected by the mirrored surface 24 can be redirected and angled so as to prevent crossing of the light rays that come from individual SPR sensors, and can lead to a number of signal outputs from the SPR layer 22.

Figure 3:
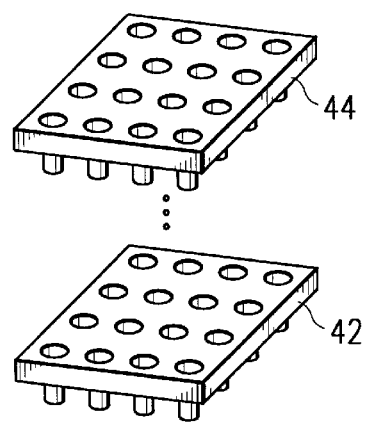
FIG. 3 is an integrated high throughput SPR sensor system.

FIG. 3 is a high throughput SPR sensor subarray system 40, which is used to detect the contents of individual wells 42 of plates 44. The individual sensors of SPR sensor subarray 10 are depicted as sensor array 46 that are able to contact the contents of wells 42. By using a single SPR sensor subarray 10 to detect the contents of all or a portion of the wells 42 in a plate 44, parallel high throughput sample analysis can be achieved. The output from the SPR sensor subarray 10 can be transferred to a computer 50 though a connection 48.

In operation, a previously baselined SPR sensor subarray 10 can be used once, or in a multiple-use embodiment several times, to analyze the interaction between test entities in wells 42 and the target layer of the protrusions 46 that form the individual sample measuring portions of the SPR sensor subarray 10. If its a single use SPR sensor subarray 10, it can be replaced after each use. Alternatively, a multiple use SPR sensor subarray can be allowed to recover prior to the next baselining event or stage. The high throughput SPR sensor subarray system 40 has the advantage of avoiding the need to have complex robotics and fluidics, while still providing the required high throughput analysis of samples using an SPR-based sensor subarray system. High throughout is achieved by measuring the interaction parameters of multiple samples concurrently.

By "dipping" the SPR sensor subarray 10 into the test entities or samples in wells, the embodiment depicted in FIG. 3 allows for the same sample in the well to be retested in subsequent steps using, e.g., a more specific analysis and detection system. Furthermore, the sample is not destroyed and can be stored for future reference. The level of contamination is also reduced, as the sample does not have to traverse a fluid exchange system prior to reaching the SPR sensor subarray 10, and after the detection event.

Figure 4:
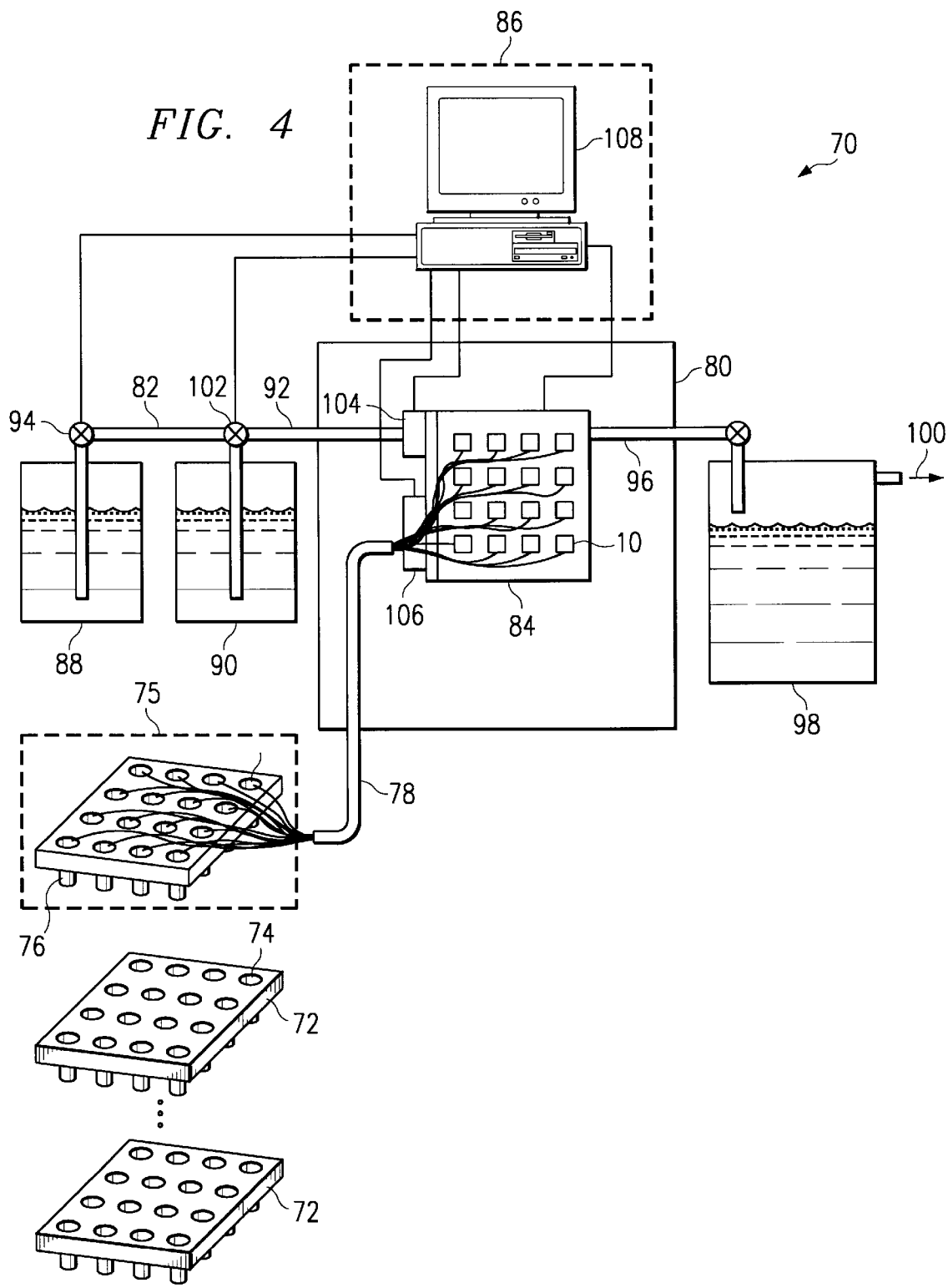
FIG. 4 depicts another embodiment of a high throughput SPR sensor array.

FIG. 4 is an integrated high throughput SPR sensor system 70 with fluidics and inline baseline and recovery system. The integrated high throughput SPR sensor system 70 is able to detect the contents of plates 72 by drawing small portions of individual samples located within wells 74 into a sample fluidics unit 75. The SPR sensor subarray 10 is reused in this embodiment for multiple analysis cycles, depending on the materials and binding characteristics of the target layer on the target layer area and the target element in a sample.

One advantage of the embodiment depicted in FIG. 4 is that it provides high throughput determination of interaction parameters will full automation, or multiple samples, in real-time. It also provides for multiple use of the SPR sensor subarray 10 and the concurrent baselining, detection and recovery of all or part of an SPR sensor subarray 10. By concurrently baselining, detecting and recovering an SPR sensor subarray 10, the period of time between baselining, detecting and recovering is reduced dramatically as compared to single or even dual detector systems that have the same baseline, detection and recovery periods. Furthermore, the use of SPR sensor subarray disclosed herein has the added advantage that temperature effects on the individual sensors during multiple detection periods are eliminated as baselining and detecting occur at the same time, at relatively the same temperature. Furthermore, a temperature control unit can be added to further control the SPR sensor subarray temperature, e.g., to increase or decrease the binding kinetics by selecting an operating temperature that is best suited to maximize the signal to noise ratio.

As will be apparent to those who are skilled in the art, less than a whole plate pipette system can be used as the portion of the sample fluidics unit 75. For example, a pipette system can be used that steps through rows or columns and withdraws small portions of samples from the plate 72, such as horizontal, vertical, single, dual or multiple well-line arrays. The sample fluidics unit 75 draws small portions from individual wells 74 through small tubes or needles 76 that draw the small portion using, e.g., a vacuum, through tubes 78. As depicted, each of the tubes 78 reach an individual needle or tube 76, however, in ultra-high throughput systems in which detection from multiple samples is to be obtained, then one conduit 78 might reach multiple needles 76. The detector system 80 combines the sample fluidics unit 75, the array preparation and detector system 82, an SPR sensor array 84 and the data capture and analysis system 86.

In operation, solutions from vessels 88 and 90 can be used to wash and baseline the individual SPR sensors 10 of the SPR array 84. For example, the content of vessel 88 can reach the SPR array via a liquid line 92, under the control of a valve 94. The contents of vessel 88 are drawn or pushed into liquid line 92 using, e.g., vacuum, pressure or gravity. The liquid line 92 reaches the SPR array 84 and via liquid conduits within the SPR array 84 (not depicted) reach and are exposed to the individual SPR sensors 10. After contacting the SPR sensors 10 the solution(s) pass through waste line 96 into a waste vessel 98, which can also serve to provide a vacuum 100.

Once the SPR array has been washed, the SPR array 84 can be baselined using, e.g., a baselining solution from vessel 90, which reaches the SPR array 34 under the control of a valve 102. The controls of the valve 94, 102, 104, and 106 can be through a computer 108 that forms part of the data capture and analysis system 86. Alternatively, the valve 94, 102, 104, and 106 can be under the control of a separate computer control system (not depicted). Once the individual SPR sensors 10 of the SPR array 84 have reached or attained baseline, valve 106 is opened momentarily to allow fluid from tubes 78 that are drawn through needles 76 from well 74 of plate 72 onto the individual SPR sensor subarray 10 of the SPR array 84. Upon exposure of the sample from well 74 to the individual SPR sensors 10, the data from the detection event is transmitted to the data capture analysis system 86. A number of communication methods can be used to transmit data from the SPR sensors 10 to the data capture and analysis system 86, such as hard wire, rf or infrared. Following the detection event, the entire system can be reset by once again by washing the surface of the SPR sensors 10 of SPR array 84, baselining the SPR array 84, changing the plate 72 from which samples will be drawn, and once again exposing the SPR array to new samples.

Figure 5:
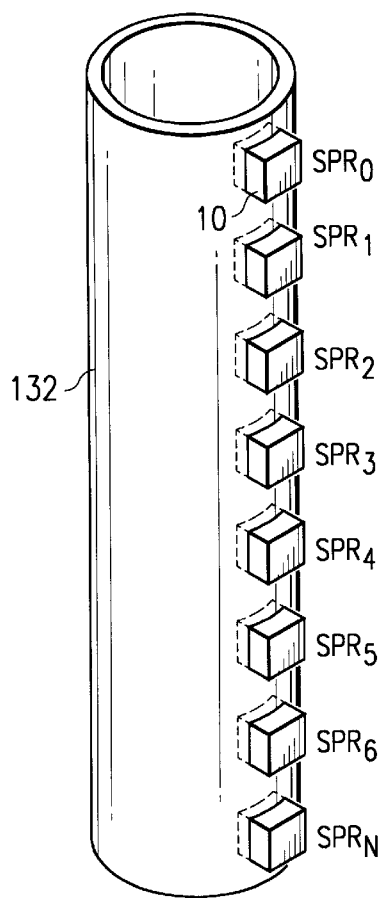
FIG. 5 depicts a variant of a high throughput SPR multiple test element analysis system.

FIG. 5 depicts, a variant of a high throughput SPR multiple SPR sensor subarray analysis system 130. A liquid line 132 has a number of SPR sensor subarrays 10 aligned in-line with the sensor surface in fluid communication with the interior of liquid line 132. This sensor array configuration allows the user wanting to detect multiple test elements within a sample concurrently, and in real-time. By setting up an array of different SPR sensor subarrays 10, the embodiment depicted in FIG. 5 can be used to determine multiple interaction parameters for a multiple of test entities in fluid communication with the SPR sensor subarray 10.

For example, a complex environmental sample containing multiple compounds of interest can be introduced into liquid line 132, with the individual SPR sensor subarrays 10 can be selected to detect each have different target layers that are specific for a class of test entities within the sample. One SPR sensor subarray 10 could contain target layers that detect different bacteria, while an adjacent SPR sensor subarray 10 could be specific for carcinogenic agents.

Figure 6:
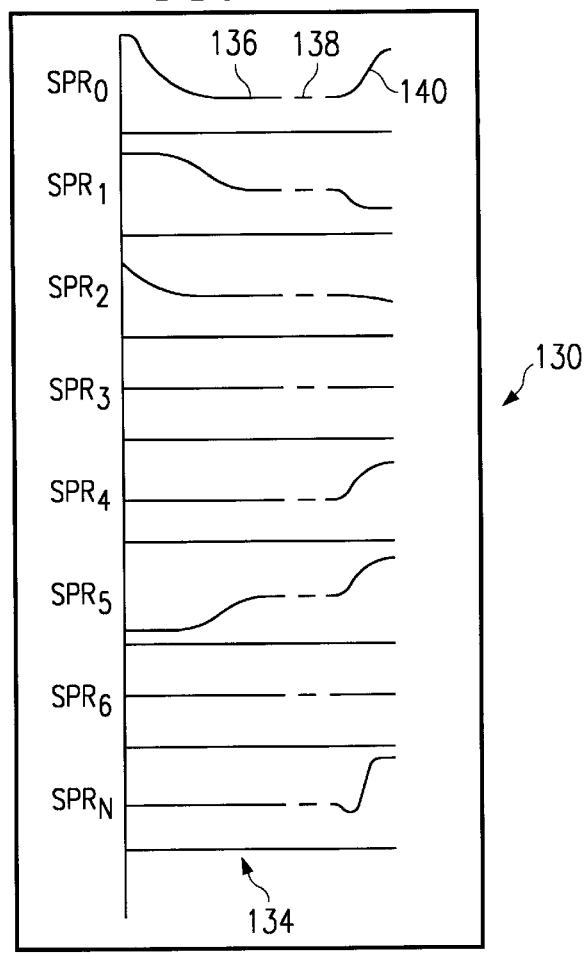
FIG. 6 depicts another variation of a high throughput SPR detection system.

FIG. 6 shows the output 134 obtained from each of the individual SPR sensors 10 that are in fluid communication with the sample in liquid line 132 depicted in FIG. 5. As can be seen, all of the sensors are first baselined at 136. For simplicity, only one of the outputs of a target layer area of an SPR sensor subarray 10 is depicted, however, each of the target layers areas could be detected, stored and analyzed separately. One way to display each of the outputs from the target layer of each SPR sensor subarray 10 could be using, e.g., color. Data could also be viewed, as is here, for only one of the target layer areas. All or some of the detectors are baselined at 136 using, e.g,. a sample buffer. Sample in buffer, pure sample or the pure buffer is added into the liquid line 132 at 138. Next, the output 140 from the individual SPR sensors 10 is measured and the presence or absence of a particular test entity to which the individual SPR sensors 10 are specific is detected. The test entity of each of the SPR sensors 10, will depend on the type of sample being analyzed, and the test entity and detection level required from the SPR sensors 10.

FIG. 7 shows another variation of a high throughput SPR detection system 150 in which SPR sensors 152 and 154 are connected to a mother board 156. The SPR sensors 152, 154 have SPR layers 158 that are depicted disposed within the well 160 that contains a sample 162. The wells can be separate or form part of a plate, such as a 6, 12, 14, 48, 96 or a 384-well plate. SPR sensor 152 can be attaining baseline, through a baselining buffer 164 while SPR sensor 154 can be within a sample containing solution 164.

Figure 8:
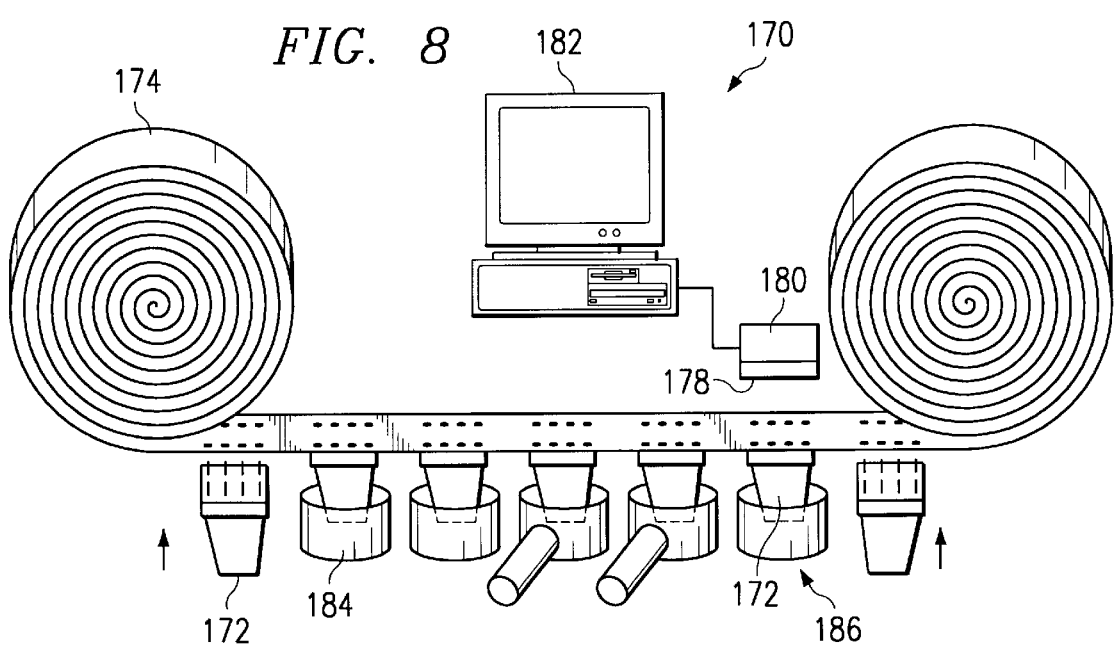
FIG. 8 depicts a single use SPR sensor subarray attached to a conveyor belt.

FIG. 8 shows a conveyor belt system 170 in which single use SPR sensors 172 are depicted being attached to a conveyor belt 174 that contain pin connectors 176 to which the single use SPR sensors 172 can be electrically connected. As with the concatenation of SPR sensors 10 depicted herein above in FIG. 4, high throughput is obtained by separating the time period for baselining into discreet concurrent detection events. The pin connectors of lead frame 28 can be attached via routing lines to pads 178 to provide an output to the external world. The pads 178 can come in contact with pads 180 that form part of a detection system which connects to, e.g., a computer 182. The pads 178 and 180 can include, e.g., a power source, ground, and an output.

As shown in operation in FIG. 8, the single use SPR sensors 172 are attached to the conveyor belt 174 and can be input or be exposed to a series of baselining chambers or liquid lines 184. Once baseline has been achieved, the single use SPR sensor 172 is exposed to a sample 186 within, e.g., a sample chamber 184 and an output detected through the pads 178 and 180 into computer 182. Following the single use test element analysis, the single use SPR sensor 172 is discarded.

Figure 9:
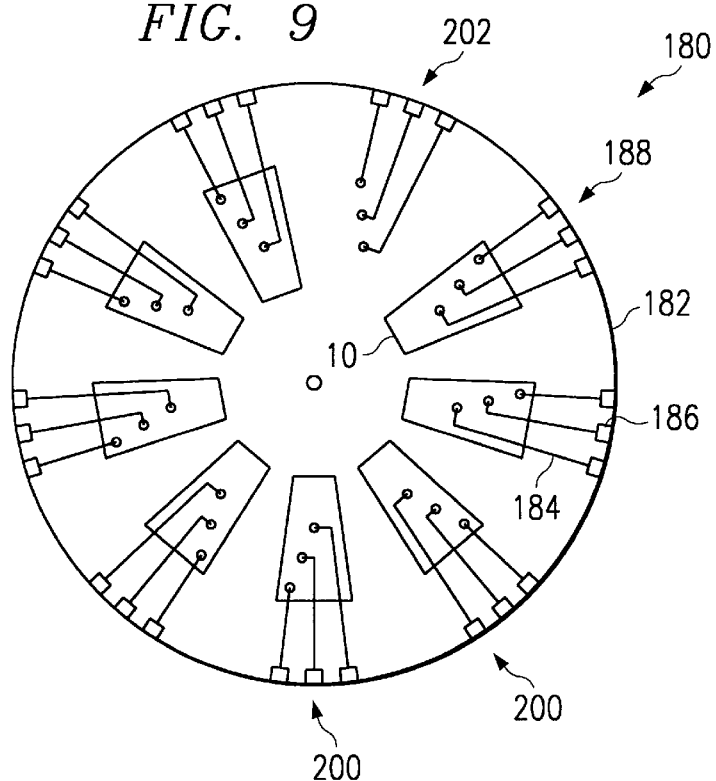
FIG. 9 depicts a high throughput lead frame disk system for use with SPR sensor subarrays.

FIG. 9 depicts a high throughput lead frame disk system for use with single use SPR sensors. As with the single use SPR sensors depicted in FIG. 9, a disk 182 has multiple routing strips 184 that lead to pads 186 which can be a power source, a ground, and an output. As with the single use SPR sensor conveyor belt system 170 FIG. 9, in operation, an SPR sensor subarray 10 is attached to disk 182 at attach station 188. As the disk is rotated clockwise, the SPR sensor subarray 10 moves onto baseline station 200, and each station baseline can be detected through the pads 186 until a baseline is obtained. The number of baseline detectors needed will depend on the throughput requirements of a detection system, as described hereinabove. The SPR sensor subarray 10 then reaches detect station 202 in which a sample has been added to the chamber where the SPR layer 22 of SPR sensor subarray 10 is exposed to the sample and the output is detected. If baseline is not attained, that individual SPR sensor can be made to go for another round of baselining without altering the system speed. Next, at detached station 190 the single use SPR sensor is removed from the disk and the disk is rotated and at attach station 188 a new SPR sensor subarray 10 is attached.

Figure 10:
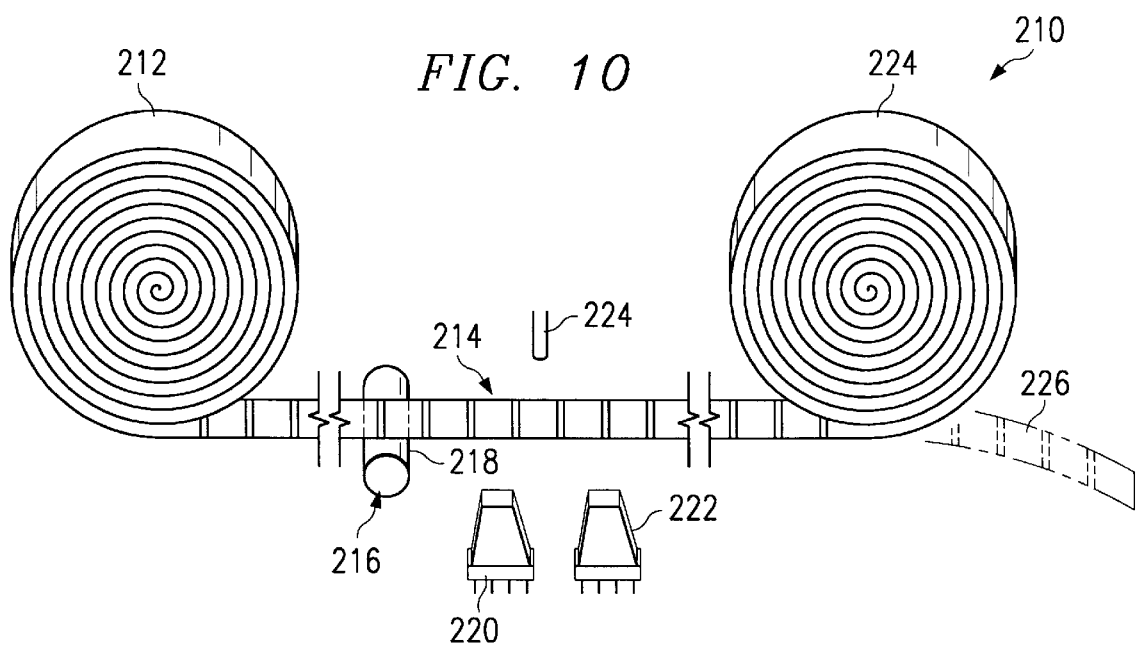
FIG. 10 depicts a reel-to-reel high throughput SPR detector surface system.

FIG. 10 shows a reel-to-reel high throughput SPR detector surface system 210. A SPR layer reel-to-reel spool 212 is made of, e.g., a very thin glass ribbon that is flexible and has on its surface an SPR layer and a target element. The SPR layer and target element form a unit 214 that is washed by exposure to washing fluid 216 at washing chamber 218. The types of washing fluids that can be used with the individual unit 214 will depend on the types analyzed and sample and can be, e.g., deionized water, a buffered solution, or a solvent. Two or more SPR sensors 220 are positioned in-line with the output of SPR layer reel-to-reel spool 212, at least one of which is a baseline sensor 220 and the other is a detector sensor 222. As with the other embodiment, one or more baselining sensor 220 can be placed before the detector sensor 222 to provide in-series baselining detection. As with the embodiments depicted in previous figures, the baselining sensor 220, or an array thereof, are used to detect when the SPR sensor surface of a unit 214 has reached a baseline, if the detection time is one minute, for example, and the average baselining time for a sample is ten minutes, then 11 baseline sensors 220 can be disposed in series and the baseline detected to match, e.g., a one minute test element analysis time. While not apparent from the figure as depicted, the individual units 214, once exposed to a wetting or wash solution 216, will generally be maintained in a humid environment chamber or exposed to a liquid. Prior to reaching the detector sensor 222, the unit 214 is exposed to a sample prior to reaching detector sensor 222. Following the detection event, the individual units 214 can either be returned to a capture reel 224, or the unit 214 can be cut into cut unit 226 for further analysis.

Figure 11:
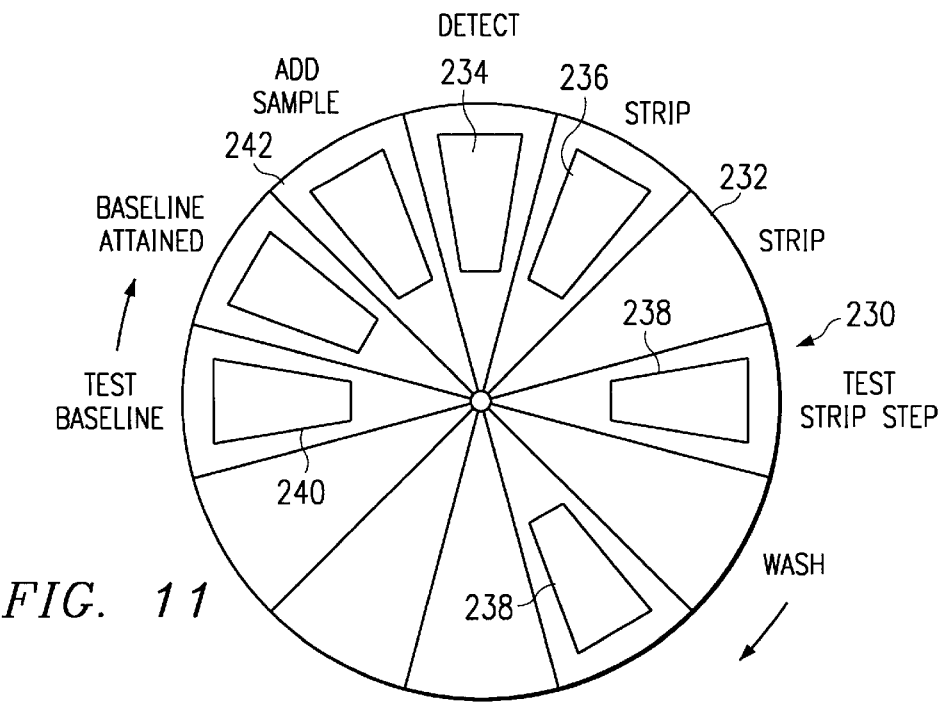
FIG. 11 depicts a high throughput disk SPR detector system.

FIG. 11 shows a high throughput disk SPR detector system in which the SPR layer 236 is reused after each detection event. A glass disk 232 has disposed thereon the SPR layer, e.g., gold, and a reusable target element. In this embodiment, three different detector sets are needed to check that the prior sample has been stripped from the target element, that baselining has been attained, and to detect the output from a new sample that is contacted with the SPR layer. Following a detection event at detection station 234, the surface of the detector area 236 is stripped of any sample. By removing the sample from the target element, the SPR detector is refurbished. Following a stripping event, the area is tested by exposing the stripped detector area 236 to a SPR strip detector, and the presence or absence of any remaining sample on the detector area 236 is determined. If sample is still found on the target element, the detector area is once again stripped in a subsequent round. The unstripped detector is not exposed to a sample when it reached the detector area and proceeds to a subsequent strip test station 238, where the removal of the test entity or sample is again determined. Using the system as described ensures that the disk continues to run without interruption. Once the detector area has been stripped, the detector area is then baselined, the detection of which occurs at baselining stations 240. Once baseline has been attained, a sample 242 is deposited on the detector area 236 and the presence or absence of a test entity that is recognized by the target element of the SPR sensor that is disposed on the surface of the disk is determined.

Figure 12:
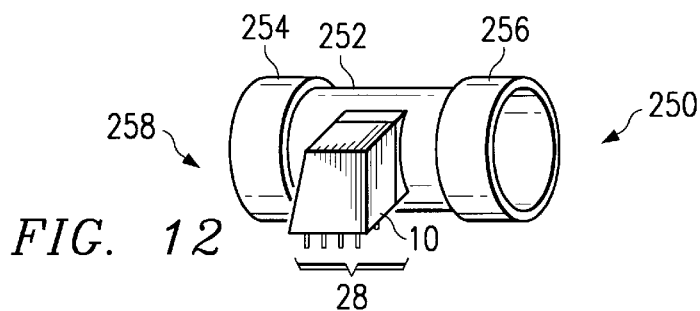
FIG. 12 depicts an embodiment of an SPR unit.
Figure 13:
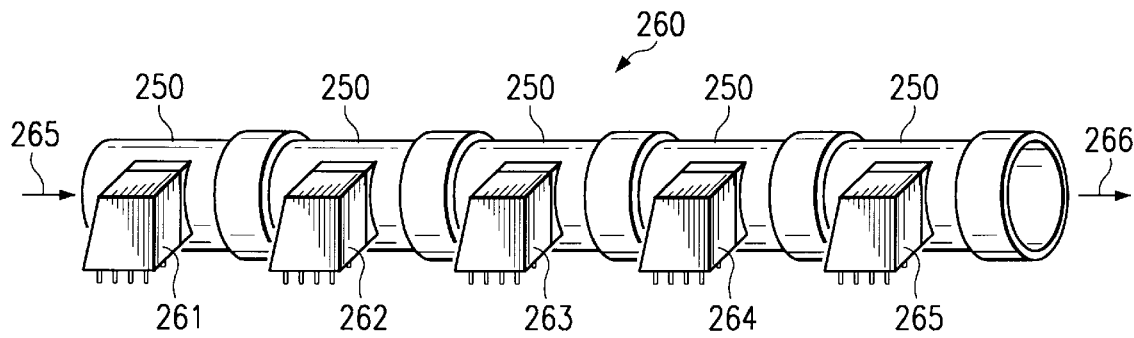
FIG. 13 depicts one or more parallel concatenated SPR sensor subarray.

FIG. 12 shows another embodiment of the present invention that allows for the rapid substitution of parallel concatenated SPR sensors. An SPR unit 250 is shown in which an SPR sensor subarray 10 is depicted having the SPR layer in communication with the inside of a chamber 252 through a window in the chamber. The chamber 252 is depicted herein as a cylinder, but any of a number of configurations are possible to promote the interaction between fluid within the chamber as the surface of an SPR sensor subarray 10 that protrudes into the chamber. A male fitting 252 and a female fitting 256 are disposed at opposite ends of the chamber 252 and permit for the rapid removal and re-attachment of an SPR unit 250 to tube connections, or as depicted in FIG. 14 to one or more SPR units 261 through 265. SPR units 261 through 265 can have different target elements disposed about the surface of the SPR layer. A fluid 258 can flow through the chamber 252 to wash and baseline the SPR sensor subarray 10, as well as provide access to a sample for detection. If an SPR unit is found to be defective, it can easily and rapidly be replaced from among other units without the need to replace the entire array of sensors.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A high throughput apparatus for determining interaction properties of test entities comprising:
   two or more SPR sensor subarrays each having at least one target element and one reference element, wherein baselined SPR sensor subarrays are used to determine interaction properties of test entities using said SPR sensor subarrays.

2. The apparatus of claim 1 wherein said SPR sensor subarrays are attached to a motherboard that permits the concurrent handling of said SPR sensor subarrays.

3. The apparatus of claim 1 wherein said SPR sensor subarrays are concurrently exposed to a baselining solution to attain baseline.

4. The apparatus of claim 1 wherein said SPR sensor subarrays comprise a target layer that interacts with said test entity to produce a change in surface plasmon resonance.

5. The apparatus of claim 1 wherein said SPR sensor subarrays are positioned to form an in-line array.

6. The apparatus of claim 1 wherein said SPR sensor subarrays form a two-dimensional array.

7. The apparatus of claim 1 wherein said SPR sensor subarrays form a circular array.

8. The apparatus of claim 1 wherein each SPR sensor subarrays is further defined as comprising:
   a substrate having a first and a second surface;
   a light source coupled to said first surface of said substrate;
   at least one photodetector coupled to said first surface of said substrate adjacent said light source; and
   a housing disposed on said first surface of said substrate, said housing having a surface that is subdivided into four or more target layer areas, wherein each of said target layer areas are predisposed to receive light from said light source and direct it towards a portion of said photodetector.

9. The apparatus of claim 1 further comprising a fluidics system in fluid communication with said SPR sensor subarrays, wherein said fluidics system is capable of providing a baselining solution and test entities to said SPP sensor subarrays.

10. The apparatus of claim 1 wherein said test entities are drug candidates.

11. The apparatus of claim 1 wherein 96 SPR sensor subarrays are disposed to form an array.

12. The apparatus of claim 1 wherein an SPR sensor subarray may comprise:
    a chamber having first and second openings and a window, wherein said SPR sensor subarray is positioned to be in fluid communication with said chamber through said window, and a linear array of SPR sensor subarrays is formed by connecting a plurality of SPR sensor subarray by said openings.

13. The SPR sensor of claim 12 wherein said first opening has disposed thereabout a male tube fitting, and second opening has disposed thereabout a female tube fitting.

14. A high throughput apparatus for determining interaction properties of test entities comprising:
    at least two SPR sensor subarrays each having at least one target element and one reference element, wherein the SPR sensor subarrays are exposed to a solution until a baseline is attained and once said SPR sensor subarrays have reached baseline, determining interaction properties of test entities using said SPR sensor subarrays; and
    a fluidics system in fluid communication with said SPR sensor subarrays, wherein said fluidics system provides baselining and test entities to said SPR sensor subarrays.

15. The apparatus of claim 14 wherein said test entities are drug candidates.

16. The apparatus of claim 14 wherein 96 SPR sensor subarrays area disposed to form an array.

17. The apparatus of claim 14 wherein said SPR sensor subarrays are positioned in-line.

18. The apparatus of claim 14 wherein said SPR sensor subarrays form a two-dimensional array.

19. The apparatus of claim 14 further comprising:
    a data capture system connected to said SPR sensor subarrays, wherein a sample provided by said fluidics system to the SPR sensor subarrays, and the output produced by said SPR sensor subarrays, is captured by said data capture system over time.

20. A method for high throughput SPR analysis for determining interaction properties of test entities comprising the steps of:
    baselining two or more SPR sensor subarrays;
    obtaining a baseline output from said SPR sensor subarrays;

exposing said SPR sensor subarrays to one or more test entities;

measuring the test entity output from said SPR sensor subarrays; and comparing said baseline output to said test entity output from said SPR sensor subarrays over time, wherein the difference between said baseline output and said test entity output enables the determination of interaction properties between said SPR sensor subarrays and said test entities.

* * * * *